US006308353B1

(12) United States Patent
Van Steenburg

(10) Patent No.: US 6,308,353 B1
(45) Date of Patent: *Oct. 30, 2001

(54) METHOD AND APPARATUS FOR POSITIONING A PATIENT

(75) Inventor: Kip Van Steenburg, Sudbury, MA (US)

(73) Assignee: The OR Group, Inc., Batesville, IN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/289,558

(22) Filed: Apr. 9, 1999

(51) Int. Cl.$^7$ ........................................................ A61F 5/37
(52) U.S. Cl. ........................ 5/632; 5/644; 5/640; 5/645; 5/655.4; 5/911
(58) Field of Search ................................ 5/632, 640, 644, 5/645, 646, 655.3, 655.4, 911, 913; 128/870, 849, 850, 606.6, 845, 846, DIG. 20, 869, 878, 882; 602/6, 13

(56) References Cited

U.S. PATENT DOCUMENTS

D. 258,612 * 3/1981 Baturin ................................. D24/64
D. 362,913 * 10/1995 Eisenberg et al. ................. D24/190

(List continued on next page.)

FOREIGN PATENT DOCUMENTS

| 1 215 859 | * | 10/1961 | (DE) . |
| 2 018 605 | * | 4/1970 | (DE) . |
| 1095311 | * | 12/1967 | (EP) . |
| 926722 | * | 5/1963 | (FR) . |
| 1437194 | * | 6/1965 | (FR) . |
| 2299874 | * | 9/1976 | (FR) . |

OTHER PUBLICATIONS

Schmidt, Vacuum Arm Splints for Children—Vacuum Mattresses for Children.*
Schmidt, Rescue Service Products.*
Söhngen, First Aid & Emergency Medical Care.*
Sohngen, Stretchers—Patient Handling Equipment, May 13, 1981.*
MDI, from the Makers of the CPR Microshield, 1995.*
Vac Fix System, Fixation System for Radiotherapy Treatment.*
Jean–Michel Reibel, GBF Medical, Oct. 11, 1992.*
Criti–Care, Cervical & Spinal Immobilization, p. 11, 1995.*
Cista Corporation, Pacvac Technology Offers Flexible Solutions to Permanent Situations, Jan. 1993.*
Bio–Medical Systems, Inc., Insta–Form Immobilizer.*
Dismed Inc., Easytop Surgical Moulding Mattress, 1987.*
A New Generation of Vacuum Mattress.*
MAB Enterprises, Inc., Germa Vac–Mattress.*
Hartwell Medical, Immobilize Patients Safety, Quickly, Effectively, Jan. 1990.*
Davis+Geek American Cyanamid Company, New Immobilizer from Davis+Geck.*
Hartwell Medical Corporation, Evac–U–Splint Training Guidelines.*

Primary Examiner—Terry Lee Melius
Assistant Examiner—Fredrick Conley
(74) Attorney, Agent, or Firm—Pearne & Gordon LLP

(57) ABSTRACT

A method and apparatus for positioning a patient for a medical procedure. The apparatus includes an air-impervious casing having a plurality of sections adapted to position and support the torso and limbs of a patient. A plurality of compartments containing beads are disposed in the sections. A plurality of connection ports are provided through which air may be evacuated from the compartments to form vacuums therein. When air is evacuated from the compartments, the beads compact together, thereby making the sections rigid.

33 Claims, 9 Drawing Sheets

U.S. PATENT DOCUMENTS

| | | |
|---|---|---|
| 3,212,497 | 10/1965 | Dickinson . |
| 3,428,973 * | 2/1969 | Hargest et al. . |
| 3,608,961 * | 9/1971 | Von Heck . |
| 3,650,523 | 3/1972 | Darby, Jr. . |
| 3,689,945 * | 9/1972 | Laerdal . |
| 3,745,998 * | 7/1973 | Rose .......................................... 602/6 |
| 3,762,404 | 10/1973 | Sakita . |
| 3,845,945 | 11/1974 | Lawley et al. . |
| 3,851,644 | 12/1974 | Slagle . |
| 3,866,606 * | 2/1975 | Hargest . |
| 4,039,039 | 8/1977 | Gottfried . |
| 4,045,830 * | 9/1977 | Loeb et al. . |
| 4,213,213 * | 7/1980 | Burnett . |
| 4,234,982 * | 11/1980 | Bez et al. . |
| 4,261,349 | 4/1981 | Lambson et al. . |
| 4,327,046 | 4/1982 | Davis et al. . |
| 4,493,877 * | 1/1985 | Burnett . |
| 4,657,003 | 4/1987 | Wirtz . |
| 4,807,618 | 2/1989 | Auchinleck et al. . |
| 4,848,364 | 7/1989 | Bosman . |
| 4,885,811 | 12/1989 | Hayes . |
| 4,898,491 | 2/1990 | Van Steenburg . |
| 4,940,218 | 7/1990 | Akcelrod . |
| 4,991,230 | 2/1991 | Vacanti . |
| 5,009,318 * | 4/1991 | Lepinoy . |
| 5,103,517 * | 4/1992 | Krouskop . |
| 5,121,756 | 6/1992 | Koledin . |
| 5,154,185 * | 10/1992 | Latimer et al. ....................... 128/870 |
| 5,159,921 | 11/1992 | Hoover . |
| 5,240,135 * | 8/1993 | Lepinoy . |
| 5,399,152 | 3/1995 | Habermeyer et al. . |
| 5,556,169 | 9/1996 | Parrish et al. . |
| 5,618,263 | 4/1997 | Alivizatos . |
| 5,626,150 | 5/1997 | Johnson et al. . |
| 5,718,669 | 2/1998 | Marble . |
| 5,826,583 | 10/1998 | Wood . |
| 5,855,207 | 1/1999 | Moenning et al. . |
| 5,906,205 * | 5/1999 | Hiebert ................................ 128/845 |

\* cited by examiner

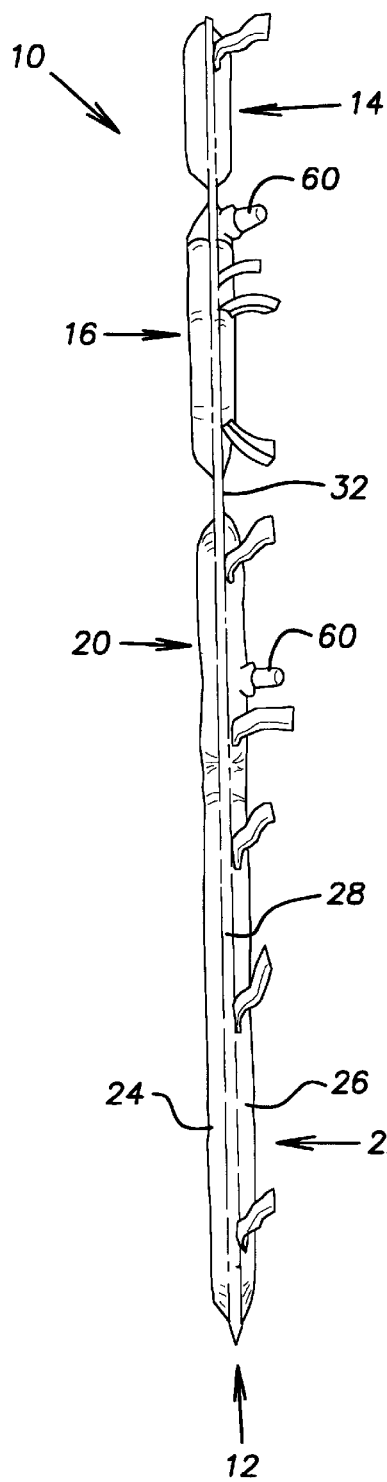
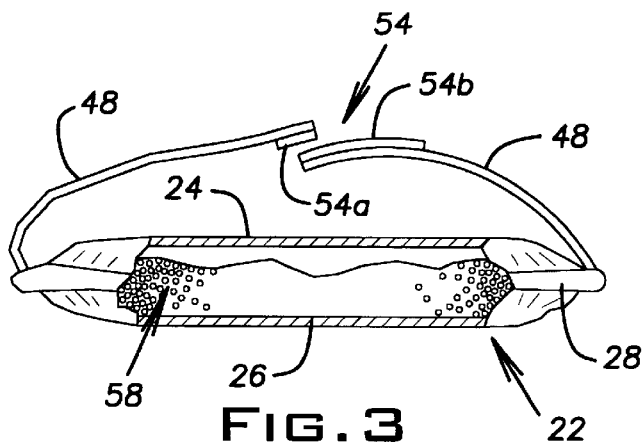
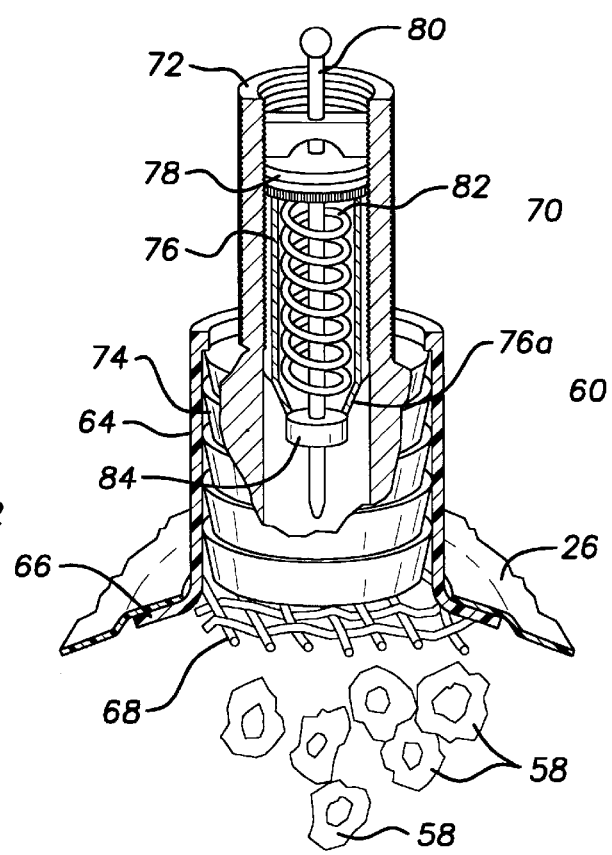
FIG. 2
FIG. 3
FIG. 4

METHOD AND APPARATUS FOR POSITIONING A PATIENT

BACKGROUND OF THE INVENTION

This invention relates to positioners in general and, more particularly, to adjustable positioners for positioning patients for medical procedures.

Many medical procedures require that a patient's body or portion thereof, such as a limb, or limbs, be positioned in a particular manner. One common method for positioning a body part is to simply have an assistant hold the body part in a desired position, and change the position when requested by the physician or surgeon. As can be appreciated this method is tiring for the assistant. In addition, this method may not support the patient's body part in a sufficiently precise and rigid manner for the medical procedure. Moreover, if more than one body part needs to be positioned, several assistants have to be utilized, which is inefficient and crowds the work area around the patient.

Other methods for positioning a body part utilize adjustable mechanical positioners. One common adjustable positioner is a sling that is attached to a body part and is connected by cables and pulleys to a ceiling, a free-standing support, or a boom extending from an operating table. These types of positioners are difficult to set up and take down, clumsy to adjust, and often obstruct the work area around the patient.

In the field of obstetrics and gynecology, a chair or table with movable leg stirrups is typically used to adjustably position the lower portion of a patient. The stirrups, however, typically have a limited range of movement and, thus, can only support the legs of a patient in a limited number of positions. Moreover, such chairs or tables are specialized and have limited utility in other medical fields.

In the field of orthopedics, a limb positioner pivotally attached to a table or chair is often used to position the arm or leg of a patient. Such a limb positioner, however, has a limited range of movement and, thus, can only support the arm or leg of a patient in a limited number of positions. Moreover, only one such limb positioner can typically be used at a time, thereby preventing a plurality of limbs from being positioned at one time.

Based on the foregoing, there is a need in the art for an improved method and apparatus for positioning patients for medical procedures, wherein the apparatus is easy to set up and take down, can support a plurality of limbs in an infinite number of positions, is simple to adjust, does not obstruct the work area around the patient, and can be used in a variety of medical fields. The present invention is directed to such a method and apparatus.

SUMMARY OF THE INVENTION

It therefore would be desirable, and is an advantage of the present invention, to provide a positioning apparatus for positioning a patient for a medical procedure. The positioning apparatus includes an air-impervious casing having a plurality of sections with compartments formed therein. The compartments are sealed from each other to prevent air flow therebetween. A plurality of beads are disposed in the compartments. A plurality of connection ports are provided through which air may be evacuated from the compartments to form vacuums therein. When the compartments are not at a vacuum, the beads in the compartments are free to move relative to each other, and when the compartments are at a vacuum, the beads in the compartments are compacted together.

Also provided in accordance with the present invention is a positioning apparatus that includes an air-impervious casing having a pair of limb sections adapted to position a pair of limbs of the patient. A plurality of beads are disposed inside the casing. A connection port is provided through which air may be evacuated from inside the casing to form a vacuum therein. When a vacuum is not formed inside the casing, the beads are free to move relative to each other, thereby making the limb sections flexible and movable relative to each other, and when a vacuum is formed inside the casing, at least a portion of the beads are compacted together, thereby making at least one of the limb sections of the casing rigid.

Also provided in accordance with the present invention is a positioning apparatus that includes an air-impervious casing having a plurality of sections with compartments formed therein. A plurality of beads are disposed in the compartments. A plurality of connection ports are provided through which air may be evacuated from the compartments to form vacuums therein. A vacuum source is provided for evacuating air from the compartments, and a pressure source is provided for supplying air to the compartments. A plurality of valves are respectively connected to the connection ports. Each of the valves is operable to selectively close an associated one of the connection ports, connect the associated one of the connection ports to the vacuum source, and connect the associated one of the connection ports to the pressure source. When the compartments are not at a vacuum, the beads in the compartments are free to move relative to each other, thereby making the sections flexible, and when the compartments are at a vacuum, the beads in the compartments are compacted together, thereby making the sections rigid.

Also provided in accordance with the present invention is a positioning apparatus that includes an air-impervious casing having a torso section, and a limb section adapted to position a limb of the patient. A torso stiffener is secured to the torso section, and a limb stiffener is secured to the limb section and is movably connected to the torso stiffener. A plurality of beads are disposed inside the casing. A connection port is provided through which air may be evacuated from inside the casing to form a vacuum therein. When a vacuum is not formed inside the casing, the beads are free to move relative to each other, and when a vacuum is formed inside the casing, at least a portion of the beads are compacted together.

Also provided in accordance with the present invention is a method of positioning a patient for a medical procedure. The method includes providing a positioning apparatus including an air-impervious casing having at least first and second sections. The casing has a plurality of beads disposed therein. The first section of the casing is secured to a first portion of the patient, and the second section of the casing is secured to a second portion of the patient. The first and second sections are moved relative to each other. Air is then removed from inside the casing to form a vacuum therein. The vacuum causes at least a portion of the beads inside the casing to compact together, thereby making at least one of the first and second sections of the casing rigid.

BRIEF DESCRIPTION OF THE DRAWINGS

The features, aspects, and advantages of the present invention will become better understood with regard to the following description, appended claims, and accompanying drawings where:

FIG. 2 shows a side view of the first embodiment of the positioning apparatus;

FIG. 3 shows a partially broken-away end view of a leg section of the first embodiment or a third embodiment of the positioning apparatus;

FIG. 4 shows a cross-sectional view of a valve mounted in a connection port of the positioning apparatus;

DETAILED DESCRIPTION OF THE PREFERRED EMBODIMENTS

Figure 1:
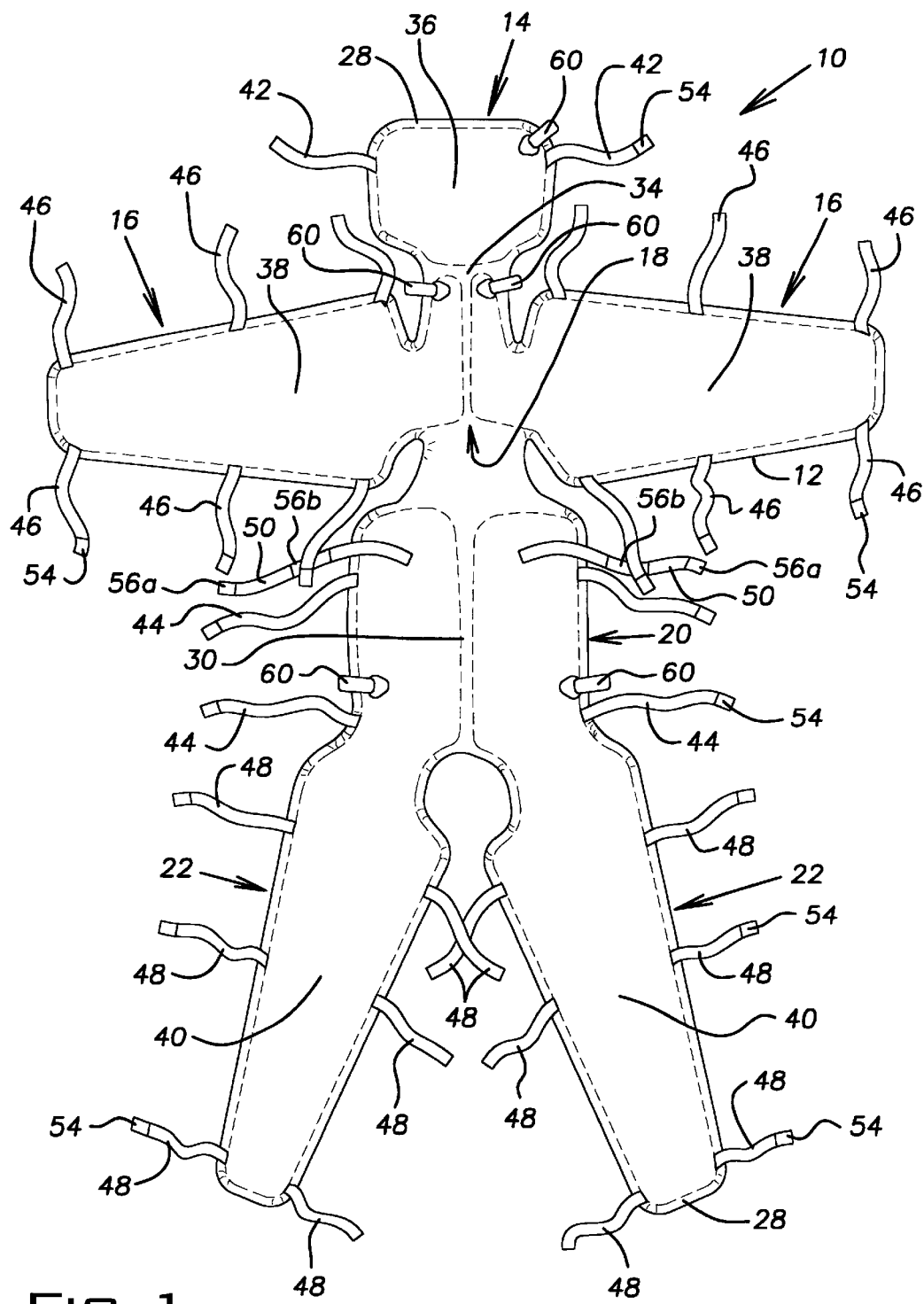
FIG. 1 shows a rear view of a first embodiment of a positioning apparatus.

It should be noted that in the detailed description which follows, identical components have the same reference numerals, regardless of whether they are shown in different embodiments of the present invention. It should also be noted that in order to clearly and concisely disclose the present invention, the drawings may not necessarily be to scale and certain features of the invention may be shown in somewhat schematic form.

Referring now to FIGS. 1 and 2, there is shown a positioning apparatus 10 constructed in accordance with a first embodiment of the present invention. The positioning apparatus 10 includes a casing 12, generally having the shape of a human body. The casing 12 has a head section 14, a pair of arm sections 16, an upper torso section 18, a lower torso section 20, and a pair of leg sections 22.

The head section 14 is generally rectangular, with its width being greater than its height. The upper torso section 18 is narrower than the head section 14 and is joined to a lower portion of the head section 14, as well as to inner portions of the arm sections 16. The inner portions of the arm sections 16 are narrow to permit the arm sections 16 to be facilely bent or otherwise moved relative to the upper torso section 18.

As the arm sections 16 extend outwardly from the inner portions, the arm sections 16 expand into enlarged shoulder portions, and then narrow into outer end portions. In this manner, each arm section 16 has a generally trapezoidal shape, with the arm section 16 narrowing as it extends outwardly so as to conform to the narrowing dimension of a human arm. The shape, the length and the width of the arm sections 16, and the separation of the arm sections 16 provided by the upper torso section 18 are selected to permit the arm sections 16 to conform to, position, and support the arms of a patient.

The lower torso section 20 is substantially wider than the upper torso section 18 and extends upwardly to just below the arm sections 16. The lower torso section 20 is joined to a lower portion of the upper torso section 18, as well as to inner portions of the leg sections 22. The inner portions of the leg sections 22 are narrow to permit the leg sections 22 to be facilely bent or otherwise moved relative to the lower torso section 20.

As the leg sections 22 extend outwardly from the inner portions, the leg sections 22 expand into enlarged thigh portions, and then narrow into outer end portions. In this manner, each leg section 22 has a generally trapezoidal shape, with the leg section 22 narrowing as it extends outwardly so as to conform to the narrowing dimension of a human leg. The shape, the length and the width of the leg sections 22, and the separation of the leg sections 22 provided by the lower torso section 20 are selected to permit the leg sections 22 to conform to, position, and support the legs of a patient.

The length of the upper torso section 18 and the length of the lower torso section 20 are selected to provide sufficient separation between the arm sections 16 and the leg sections 22 to permit the arm sections 16 to position and support the arms of a patient, while the leg sections 22 position and support the legs of a patient.

As shown best in FIG. 2, the casing 12 is formed from an inner or front panel 24, and an outer or rear panel 26, each of which has the same general shape of a human body. The front and rear panels 24, 26 are composed of an air-impervious material. Preferably, the air-impervious material is a flexible thermoplastic material so as to permit the front and rear panels 24, 26 to be heat-sealed together. Flexibility is important to permit the casing 12 to conform to a patient's body, and to permit the casing 12 to be bent, twisted, and otherwise manipulated when the patient's body is being moved to a desired position. Suitable thermoplastic materials include soft polyvinyl chloride, nylon, polypropylene, polyethylene, fluoropolymers, urethane, copolymers of ethylene and vinyl acetate, silicon rubber, and mixtures of polyvinyl chloride and synthetic rubber. The thermoplastic material may also be composed of a composite, such as a woven nylon material with a protective coating of urethane or vinyl.

The front and rear panels 24, 26 are joined together at their mating peripheries by a peripheral seal 28. The front and rear panels 24, 26 are also joined together in the upper and lower torso sections 18, 20 by a central longitudinal seal 30, a middle transverse seal 32, and an upper transverse seal 34. The peripheral seal 28, the longitudinal seal 30, and the middle and upper transverse seals 32, 34 may be formed by heat sealing and are arranged so as to form a head compartment 36, a pair of arm compartments 38, and a pair of leg compartments 40. The head, arm, and leg compartments 36–40 are sealed from each other to prevent air flow therebetween.

The head compartment 36 occupies substantially all of the head section 14 and is separated from the arm compartments 38 by the upper transverse seal 34. Each arm compartment 38 occupies substantially all of its respective arm section 16, and occupies about half of an upper portion of the upper torso section 18. The portions of the arm compartments 38 occupying the upper torso section 18 are separated by the longitudinal seal 30. The arm compartments 38 are separated from the leg compartments 40 by the middle transverse seal 32, which is enlarged and comprises most of the lower portion of the upper torso section 18. Each leg compartment 40 occupies substantially all of its respective leg section 22, and occupies about half of the lower torso section 20. The portions of the leg compartments 40 occupying the lower torso section 20 are separated by the longitudinal seal 30.

At least one pair of head straps 42 is secured to the rear panel 26 at the peripheral seal 28, on opposing sides of the head section 14, and pairs of body straps 44 are secured to the rear panel 26 at the peripheral seal 28, on opposing sides of the lower torso section 20. Pairs of arm straps 46 are secured to the rear panel 26 at the peripheral seal 28, on opposing sides of each of the arm sections 16, and pairs of leg straps 48 are secured to the rear panel 26 at the peripheral seal 28, on opposing sides of each of the leg sections 22. At least one pair of anchor straps 50 are secured to the rear panel 26 in the lower torso section 20, at a position spaced inwardly from the peripheral seal 28.

The head, body, arm, and leg straps 42–48 are preferably composed of a strong fabric, such as a nylon fabric, and are of sufficient length to permit the pairs of head, body, arm, and leg straps 42–48 to form loops that can be disposed around body parts of patients of different sizes. Preferably, the pairs of head, body, arm, and leg straps 42–48 are provided with fasteners 54 to secure the loops in position. In this manner, the head, body, arm, and leg straps 42–48 are used to secure body parts of a patient to the head section 14, the lower torso section 20, the arm sections 16, and the leg sections 22 of the positioning apparatus 10.

As best shown in FIG. 3, the fasteners 54 may be hook and eye, or more preferably buckles, or still more preferably male pieces 54a of "Velcro" and female pieces 54b of "Velcro" respectively secured to the ends of opposing straps. "Velcro" is a registered trademark of Velcro Industries, B.V., identifying hook and loop-type fasteners. The female pieces 54b are preferably elongated to permit adjustable securement of opposing straps, which, in turn, permits the diameters of the loops to be adjusted to accommodate body parts of patients of different sizes.

The number of pairs of head, body, arm, and leg straps 42–48 and their positioning are selected to enable the head, arm, lower torso, and leg sections 14, 16, 20, 22 of the positioning apparatus 10 to be secured to body parts without any looseness or buckling at the ends or midsections of the head, arm, lower torso, and leg sections 14, 16, 20, 22. As shown, there may be one pair of head straps 42, three pairs of arm straps 46 for each arm section 16, three pairs of leg straps 48 for each leg section 22, and two pairs of body straps 44.

The anchor straps 50 are sufficiently long to permit each anchor strap 50 to extend laterally from the positioning apparatus 10 and form a loop around a structure, such as a bar, disposed proximate to the positioning apparatus 10. Each anchor strap 50 is provided with a fastener 56 to secure the anchor strap 50 in the loop. The fastener 56 may be a hook and eye, or more preferably a buckle, or still more preferably a male piece 56a of "Velcro" and a female piece 56b of "Velcro" secured to a surface of the anchor strip 50 as shown in FIG. 1. The female piece 56b is spaced sufficiently from the male piece 56a and is sufficiently long to permit the diameter of the loop formed by the anchor strap 50 to be adjusted to accommodate different types of structures.

The head compartment 36, the arm compartments 38, and the leg compartments 40 are each partially filled with a large number of small lightweight granules or beads 58 (shown in FIGS. 3 and 4) that pack together to form a rigid mass when subjected to a vacuum. The beads 58 should be sufficiently rigid to withstand the stresses that occur when the beads 58 engage each other upon application of a vacuum, and should have a high mechanical strength to prevent the beads 58 from fracturing or breaking apart after repeated use of the positioning apparatus 10. In addition, the beads 58 should be elastically deformable to permit the beads 58 to pack together tightly when a vacuum is applied.

The beads 58 may be composed of solid or expanded plastic material. Preferably, the beads 58 are composed of expanded polystyrene or polyvinyl chloride because expanded polystyrene and polyvinyl chloride have high mechanical strength, elastic deformability, and low specific gravity. More preferably, the beads 58 are composed of expanded polystyrene.

Preferably, the beads 58 have a diameter in a range from about 1 mm to about 10 mm, more preferably from about 5 mm to about 10 mm. The beads 58 may have a uniform size and shape, or a variety of sizes and shapes. It is believed that beads 58 having a variety of sizes and shapes provide more uniform and stable support. In addition, commercially available beads 58 tend to have a variety of sizes and shapes. Accordingly, it is preferred if the beads 58 have a variety of sizes and shapes. Preferably, the beads 58 have a low density, in the range of about 0.5 lbs/ft$^3$ to about 2.0 lbs/ft$^3$, more preferably from about 1 lb/ft$^3$ to about 2.0 lbs/ft$^3$; these ranges being given for the bulk density of a given volume of beads 58 packed together without compression.

The beads 58 are freely and loosely packed into the head compartment 36, the arm compartments 38, and the leg compartments 40, so as to permit the beads 58 to move relative to each other when the head, arm, and leg compartments 36–40 are in collapsed modes, i.e., at about atmospheric pressure. In this manner, the positioning apparatus 10 can be facilely manipulated to conform to, and position, a patient's body when the head, arm, and leg compartments 36–40 are in collapsed modes.

Figure 5:
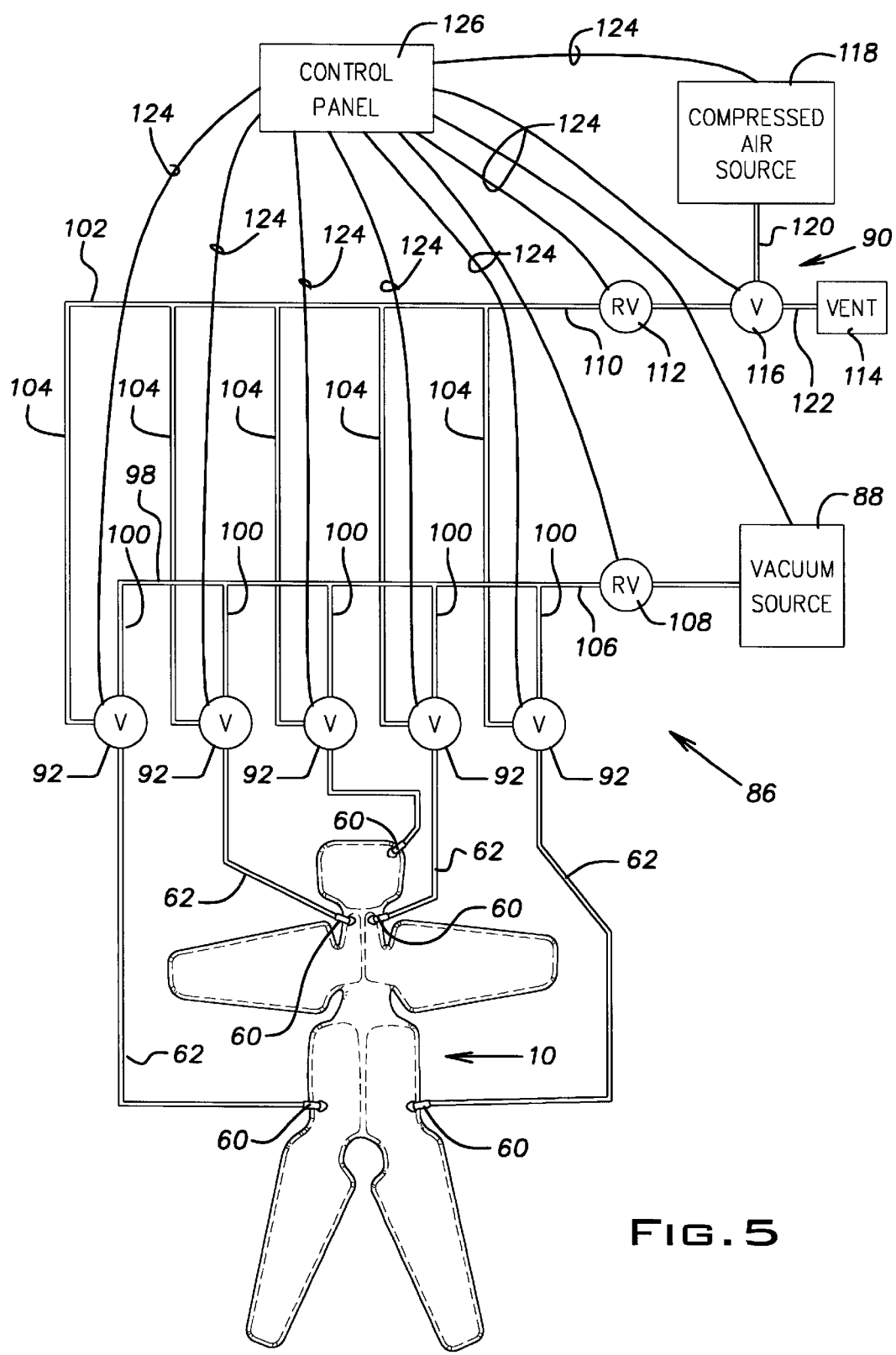
FIG. 5 shows a schematic view of the first embodiment of the positioning apparatus connected by a valve complex to a vacuum source and a pressure source.
Figure 6:
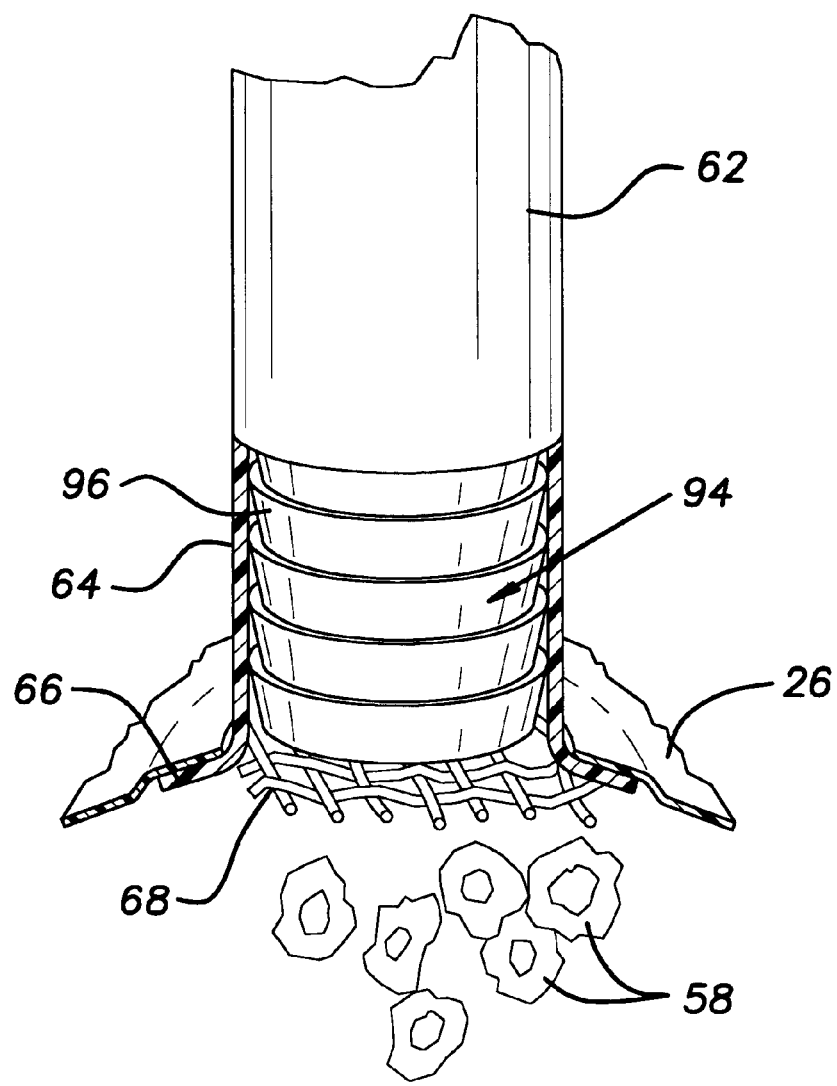
FIG. 6 shows a partial cross-sectional view of a pneumatic line connected to a connection port of the positioning apparatus.
Figure 7:
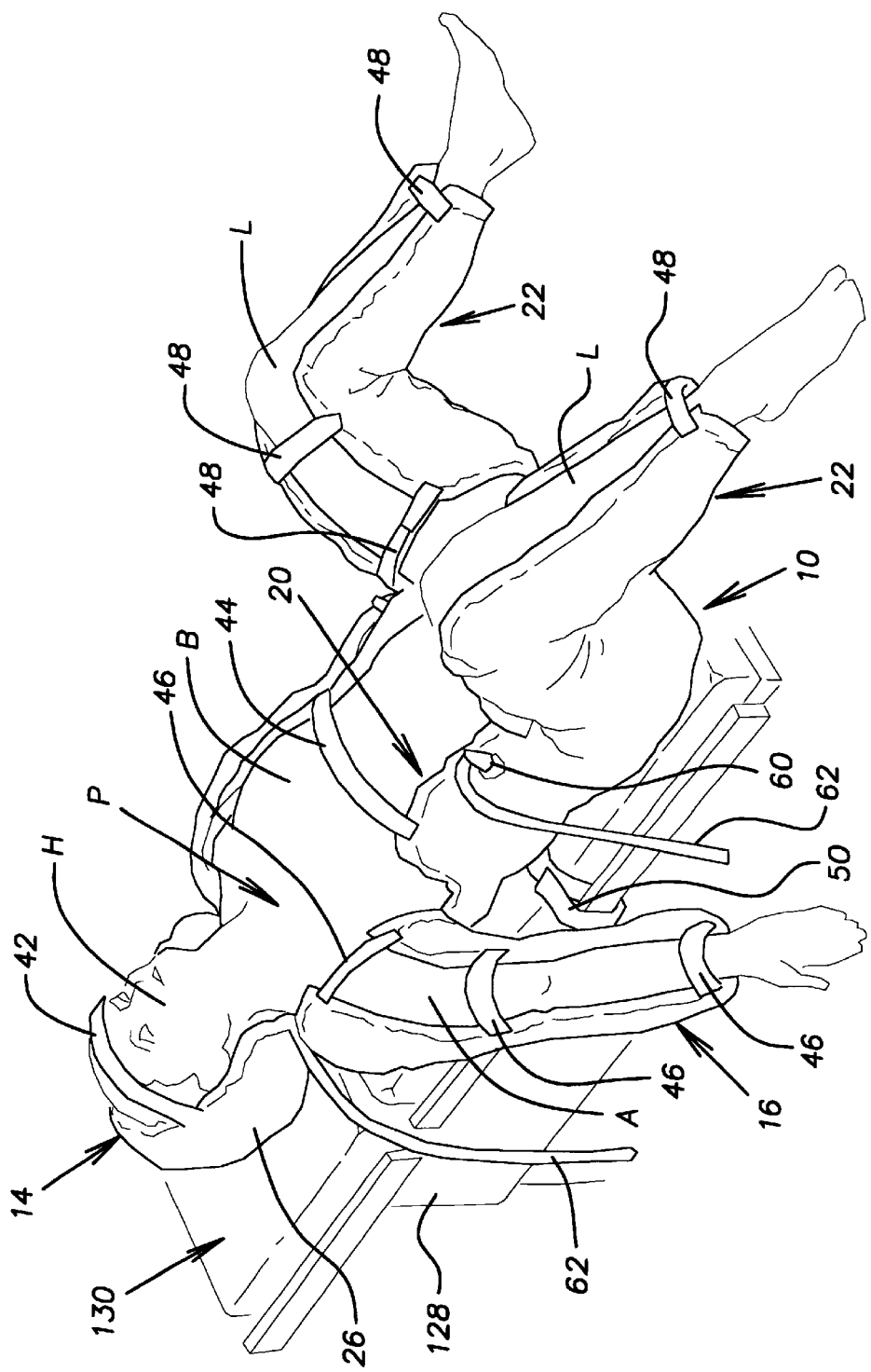
FIG. 7 shows a front perspective view of the first embodiment of the positioning apparatus being used to position a patient.

Referring now to FIG. 4, the head, arm, and leg compartments 36–40 have connection ports 60 for connecting the head, arm, and leg compartments 36–40 to pneumatic lines 62 (shown in FIGS. 5–7). Each of the connection ports 60 includes a tubular sleeve 64 having an inner end joined to an annular base 66. The sleeve 64 and the base 66 are preferably composed of a thermoplastic elastomer, such as a styrene copolymer, a polyurethane copolymer, or a polyester. The sleeve 64 extends through an opening in the rear panel 26 of the casing 12. The base 66 is joined around the opening to an inner surface of the rear panel 26, such as by heat sealing. A layer of fine mesh wire screen 68 is secured to the base 66, over the opening. The screen 68 has openings sufficiently small to prevent beads 58 from passing therethrough. In this manner, the screen 68 prevent beads 58 from being drawn through the sleeve 64 when a vacuum is applied to the sleeve 64.

The connection ports 60 are located in the rear panel 26 of the casing 12, toward the peripheral seal 28 so as to avoid contact with the body of a patient. The connection port 60 for the head compartment 36 is located at the top of the head section 14, the connection ports 60 for the arm compartments 38 are located at the top of the upper torso section 18, and the connection ports 60 for the leg compartments 40 are located at the bottom of the lower torso section 20. Thus, the connection ports 60 are located in portions of the positioning apparatus 10 that typically remain stationary and are positioned close to a supporting structure, thereby permitting the pneumatic lines 62 to be positioned away from the work space around the patient so as to not interfere with medical personnel.

Each of the connection ports 60 may be provided with a valve 70, as shown. The valve 70 is preferably a Schrader valve, which is commonly used in the tire industry. The valve 70 includes a body 72 having a series of outer step-tapered wedging rings 74 to enable the body 72 to be set firmly into the sleeve 64 without leakage occurring. A tubular insert 76 is threadably disposed in the body 72 and includes a tapered bottom end 76a and an upper end with a blocking member 78 secured thereto. A stem 80 extends through the insert 76 and the blocking member 78, and is urged upwardly by a spring 82 acting against the blocking member 78. When the spring 82 is in its normal position biasing the stem 80 to an upper limit, the bottom end 76a of the insert 76 is engaged by a valve seat 84 disposed about the stem 80. When the stem 80, however, is depressed as by attachment of a fitting to draw a vacuum or inject air, a wide opening is presented between the bottom end 76a of the insert 76 and the valve seat 84, thereby permitting the passage of air in either direction.

Referring now to FIG. 5, the connection ports 60 may be connected to a valve complex 86 for selectively closing the connection ports 60, connecting the connection ports 60 to a vacuum source 88, and connecting the connection ports 60 to a pressure source 90. If the connection ports 60 are connected to the valve complex 86, it is not necessary to provide the connection ports 60 with their own valves 70.

The valve complex 86 includes control valves 92, respectively connected by the pneumatic lines 62 to the connection ports 60. The pneumatic lines 62 have first ends adapted for connection to the control valves 92 and second ends adapted for connection to the connection ports 60. If the connection ports 60 are provided with their own valves 70, the second ends of the pneumatic lines 62 are provided with couplings (not shown) for securing the pneumatic lines 62 to the bodies 72 of the valves 70 and for depressing the stems 80 of the valves, thereby opening the valves 70. If the connection ports 60 are not provided with their own valves 70, the connection ports 60 may be directly connected to the pneumatic lines 62 by insertion-type connectors 94 (shown in FIG. 6), each of which is elongated and hollow, with opposing ends having outer step-tapered wedging rings 96. The opposing ends of the connectors 94 are respectively wedged into the sleeves 64 of the connection ports 60 and the second ends of the pneumatic lines 62.

Each of the control valves 92 is a three-way valve, having an outlet port, a vacuum port, and a pressure port. The outlet ports of the control valves 92 are connected to the connection ports 60 of the positioning apparatus 10 by the pneumatic lines 62, while the vacuum ports of the control valves 92 are connected to a first header 98 by tubes 100, and the pressure ports of the control valves 92 are connected to a second header 102 by tubes 104.

The first header 98 is connected to the vacuum source 88 by a main vacuum line 106. A regulating valve 108 may be disposed in the main vacuum line 106 to control the vacuum produced at the first header 98. The vacuum source 88 may be a portable manually-actuated vacuum pump, or a small electrical vacuum pump dedicated to the positioning apparatus 10 and located proximate to the positioning apparatus 10, or a large vacuum pump that provides a vacuum to a plurality of devices and is located remote from the positioning apparatus 10, such as in a basement of the building in which the positioning apparatus 10 is located. Preferably, the vacuum source 88 provides a vacuum of about 10 to 100 mm Hg, more preferably about 10 to 50 mm Hg, at each of the connection ports 60.

The second header 102 is connected to the pressure source 90 by a pressure line 110. A regulating valve 112 may be disposed in the pressure line 110 to control the pressure at the second header 102. The pressure source 90 may consist of an opening or vent 114 to atmospheric pressure, or the pressure source 90 may include a diverter valve 116 connected to the vent 114 and a compressed air source 118, wherein the diverter valve 116 is operable to selectively connect the second header 102 to the vent 114 and the compressed air source 118. The compressed air source 118 is connected to the diverter valve 116 by a compressed pressure line 120, while the vent is connected to the control valve by a vent line 122. The diverter valve 116 is movable between a vent position, wherein the second header 102 is connected to the vent 114, i.e., is in air flow communication with the vent 114, and a compressed pressure position, wherein the second header 102 is connected to the compressed air source 118, i.e., is in air flow communication with the compressed air source 118.

The compressed air source 118 may be a portable manually-actuated pump, or a small electric air compressor dedicated to the positioning apparatus 10 and located proximate to the positioning apparatus 10, or a large air compressor that provides compressed air to a plurality of devices and is located remote from the positioning apparatus 10, such as in a basement of the building in which the positioning apparatus 10 is located. The vacuum source 88 and the compressed air source 118 may be part of the same apparatus. An example of such an apparatus is the reciprocating piston air compressor disclosed in U.S. Pat. No. 5,551,845 to Milam, which is incorporated herein by reference. The air compressor of Milam simultaneously produces a vacuum at an intake valve thereof and compressed air at an exhaust valve thereof. Preferably, the compressed air source 118 is sized to provide a pressure at each of the connection ports 60 that is about 10 to 100 mm Hg, more preferably about 10 to 50 mm Hg above atmospheric pressure.

The control valves 92, the regulating valves 108, 112, and the diverter valve 116 may be manual valves or, more preferably, solenoid valves. If the control valves 92, the regulating valves 108, 112, and the diverter valve 116 are solenoid valves, the control valves 92, the regulating valves 108, 112, and the diverter valve 116 may be connected by wiring 124 to a control panel 126 from which the control valves 92, the regulating valves 108, 112, and the diverter valve 116 may be controlled. In this manner, the control panel 126 may be located remotely from the valve complex 86.

Each control valve 92 is movable between a closed position, a vacuum position, and a pressure position. In the closed position, the vacuum port and the pressure port are both closed, thereby closing the connection port 60 to which the control valve 92 is connected. In the vacuum position, the vacuum port is open and the pressure port is closed, thereby connecting the connection port to the vacuum source 88, i.e., placing the connection port 60 in air flow communication with the vacuum source 88. In the pressure position, the vacuum port is closed and the pressure port is open, thereby connecting the connection port to the pressure source 90, i.e., placing the connection port in air flow communication with the pressure source 90.

The operation of the positioning apparatus 10 will now be described with reference to FIG. 7. The connection ports 60 of the positioning apparatus 10 are directly connected to the pneumatic lines 62, which, in turn, are connected to the valve complex 86. The control valves 92 are in the pressure positions so as to place the connection ports 60 in air flow communication with the pressure source 90, which includes the diverter valve 116 connected to the vent 114 and the compressed air source 118. The diverter valve 116 is in the vent position. Thus, the connection ports 60 and therefore the head, arm, and leg compartments 36–40 are at atmospheric pressure, thereby permitting the beads 58 to move freely relative to each other. Accordingly, the positioning apparatus 10 can be facilely manipulated.

The positioning apparatus 10 is preferably supported on a structure, such as a table 128, with the rear panel 26 of the casing 12 contacting a top surface 130 of the table 128. The positioning apparatus 10 is secured to the table 128 by the anchor straps 50, which are securely formed into loops disposed around side bars 132 of the table 128. A patient P is placed in a supine position on top of the positioning apparatus 10 so as to the contact the front panel 24 of the casing 12. The head H, body B, arms A, and legs L of the patient P are respectively aligned over the head section 14, the upper and lower torso sections 18, 20, the arm sections 16, and the leg sections 22 of the positioning apparatus 10.

The pairs of head, body, arm, and leg straps 42–48 are secured together using the fasteners 54 so as to form loops around the head H, arms A, legs L, and body B of the patient P, thereby securing the patient P to the positioning apparatus 10. Preferably, the loops are made sufficiently tight to respectively draw the arm sections 16, the leg sections 22, and the lower torso section 20 of the positioning apparatus 10 around approximately two-thirds of the circumference of the arms A, legs L, and lower portion of the body B the patient P.

With the patient P secured to the positioning apparatus 10 as described above, medical personnel may then configure the positioning apparatus 10 to place the patient P in a desired position for a medical procedure. For example, if the medical procedure is a gynecological or obstetrical examination, the inner portions of the leg sections 22 may be bent upwardly and outwardly to spread the legs L of the patient P, and middle portions of the leg sections 22 may be bent downwardly to bend the knees of the patient P, as shown. The arm sections 16 may also be moved inwardly, toward the upper and lower torso sections 18, 20.

While the medical personnel are holding the positioning apparatus 10 in the desired configuration, the vacuum source 88 is activated and the control valves 92 are moved to the vacuum positions. As a result, the connection ports 60 are placed in air flow communication with the vacuum source 88, which draws air from the head, arm, and leg compartments 36–40 to form vacuums therein. Consequently, the beads 58 inside the head, arm, and leg compartments 36–40 compact together, thereby making the head section 14, the arm sections 16, and the leg sections 22 rigid. Once the desired rigidity is achieved, the control valves 92 are moved to the closed positions, thereby closing the connection ports 60 to maintain the vacuums in the head, arm, and leg compartments 36–40.

With the head section 14, the arm sections 16, and the leg sections 22 in rigid states, the positioning apparatus 10 supports and maintains the patient P in the desired position. The medical procedure may then be performed on the patient P.

If it is desired to change the position of a portion of the patient P, such as the leg L, the control valve 92 for the leg compartment 40 in the leg section 22 positioning the leg L is moved to the pressure position to at least partially break the vacuum in the leg compartment 40 so as to allow the leg section 22 to be moved to a new position. The control valve 92 is then moved to the vacuum position to reestablish the vacuum in the leg compartment 40 and once again make the leg section 22 rigid so as to support the leg L in the new position.

Once the medical procedure is completed, the control valves 92 are moved to the pressure positions to bring the head, arm, and leg compartments 36–40 back to atmospheric pressure, thereby permitting the beads 58 to move freely relative to each other. Consequently, the positioning apparatus 10 is once again flexible to permit the positioning apparatus 10 to be removed from the patient P.

If it is observed that clumps of beads 58 remain in the positioning apparatus 10 after the head, arm, and leg compartments 36–40 are brought back to atmospheric pressure, the diverter valve 116 may be moved to the compressed air position to introduce superatmospheric air into the head, arm, and leg compartments 36–40 so as to break up the clumps of beads 58.

When the vacuum(s) is/are released in the head, arm, and/or leg compartments 36–40 at the conclusion of the medical procedure, or to move a body part during the medical procedure, it may desirable to slowly release the vacuum(s) so as to prevent the head section 14, the arm sections 16, the upper torso section 18, the lower torso section 20, and/or the leg sections 22 from abruptly collapsing. To do so, the regulating valve 112 in the pressure line 110 is closed before a desired one, or all, of the control valves 92 is/are moved to the pressure position(s). After the control valve(s) 92 is/are moved to the pressure position(s), the regulating valve 112 is slowly opened to gradually increase the pressure(s) in the head section 14, the arm sections 16, the upper torso section 18, the lower torso section 20, and/or the leg sections 22.

It should be appreciated that if the valve complex 86 is not used, the valve 70 in the connecting port 60 of one of the head, arm, and leg compartments 36–40 may be directly connected to the vacuum source 88 by a connecting line with a coupling. In this manner, the head, arm, and/or leg compartments 36–40 may be serially evacuated by connecting the vacuum source 88 to one compartment, evacuating the compartment, and then disconnecting the vacuum source 88, then connecting the vacuum source 88 to another compartment, evacuating that compartment, and so on, until all of the desired head, arm, and/or leg compartments 36–40 are evacuated.

Figure 8:
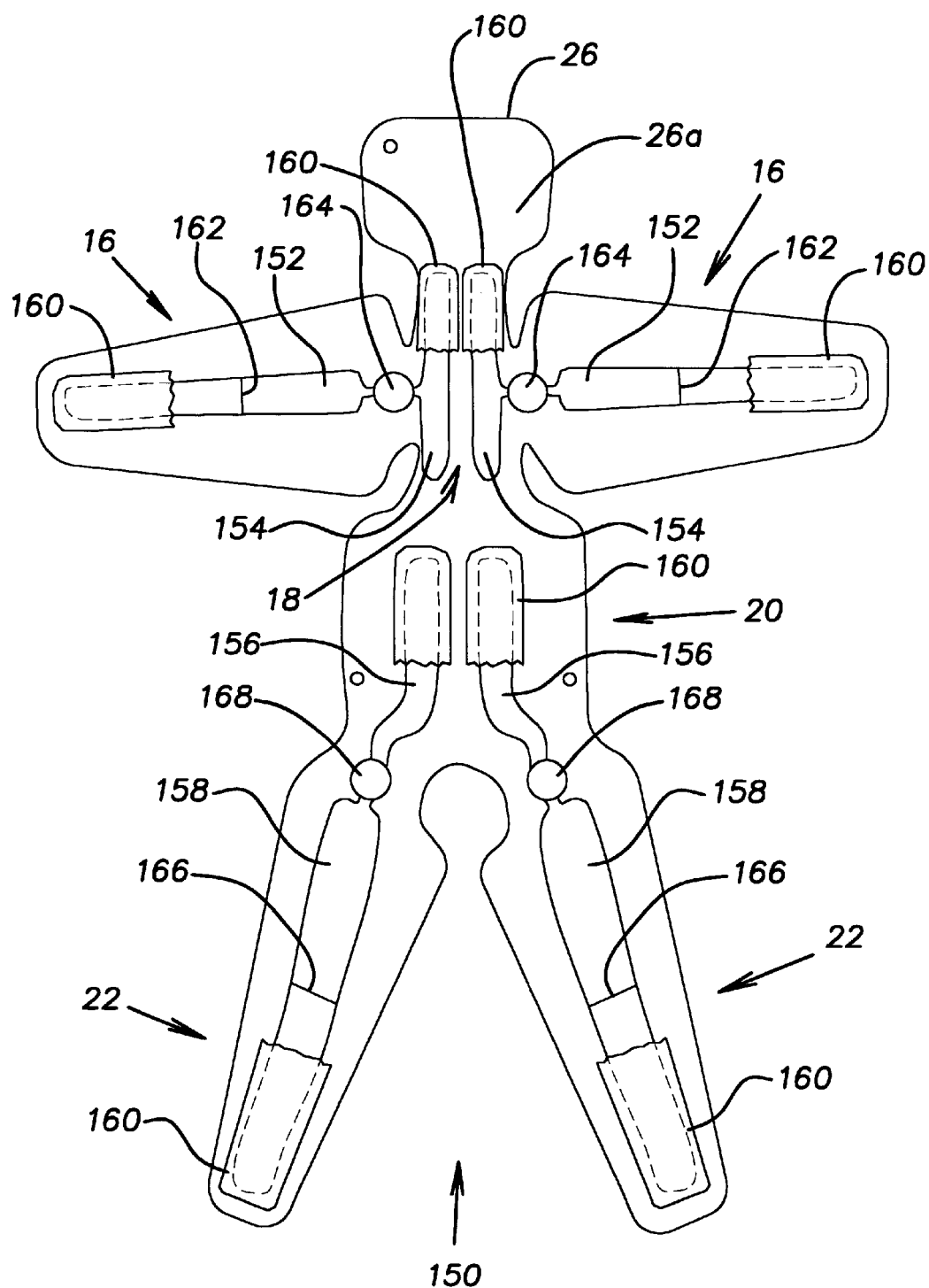
FIG. 8 shows a front view of a portion of a second embodiment of the positioning apparatus.

Referring now to FIG. 8, there is shown a second embodiment of the present invention. Specifically, FIG. 8 shows a front view of a portion of a second positioning apparatus 150 having essentially the same construction as the positioning apparatus 10 of the first embodiment shown, except for the differences to be hereinafter described. The front panel 24 and the beads 58 have been removed to better show the features of the second embodiment. The second positioning apparatus 150 includes a pair of arm stiffeners 152, a pair of upper torso stiffeners 154, a pair of lower torso stiffeners 156, and a pair of leg stiffeners 158, each of which is preferably composed of a hard plastic, such as acrylonitrile-butadiene-styrene (ABS) plastic. The arm, upper torso, lower torso, and leg stiffeners 152–158 are secured to an interior surface 26a of the rear panel 26 by securing retaining sheets 160 of a flexible material to the casing 12, over the arm, upper torso, lower torso, and leg stiffeners 152–158, thereby trapping the arm, upper torso, lower torso, and leg stiffeners 152–158 between the rear panel 26 and the retaining sheets 160. The retaining sheets 160 are shown partially broken away to better show the arm, upper torso, lower torso, and leg stiffeners 152–158. Preferably, the flexible material is the same thermoplastic material that the casing 12 is composed of.

Preferably, the upper torso stiffeners 154 are flat and generally rectangular in shape, and are disposed in the upper torso section 18. The upper torso stiffeners 154 extend longitudinally between the middle and upper transverse seals 32, 34.

Preferably, the arm stiffeners 152 are flat and generally rectangular in shape, and are disposed in, and extend longitudinally along, the arm sections 16, up to the inner portions thereof. The arm stiffeners 152 have hinges 162, located approximately midway along the lengths of the arm sections 16 so as to be aligned with the elbows of a patient. The hinges 162 may be living hinges integrally formed with the arm stiffeners 152. The arm stiffeners 152 may be connected to the upper torso stiffeners 154 by ball joints 164, as shown. The ball joints 164 are located in the inner portions of the arm sections 16 so as to be aligned with the shoulders of a patient.

Preferably, the lower torso stiffeners 156 are flat and generally rectangular in shape, and are respectively disposed in the lower torso section 20. The lower torso stiffeners 156 extend longitudinally between the middle transverse seal 32 and the leg sections 22.

Preferably, the leg stiffeners 158 are flat and generally rectangular in shape, and are disposed in, and extend longitudinally along, the leg sections 22, up to the inner portions thereof. The leg stiffeners 158 have hinges 166, located approximately midway along the lengths of the leg sections 22 so as to be aligned with the knees of a patient. The hinges 166 may be living hinges integrally formed with the leg stiffeners 158. The leg stiffeners 158 may be connected to the lower torso stiffeners 156 by ball joints 168, as shown. The ball joints 168 are located in the inner portions of the leg sections 22 so as to be aligned with the hips of a patient.

The arm, upper torso, lower torso, and leg stiffeners 152–158 function as a frame to reinforce the second positioning apparatus 150 to prevent undesired bending or sagging of the second positioning apparatus 150 when positioning a patient, especially a large patient. The hinges 162, 166 and the ball joints 164, 168, however, permit the second positioning apparatus 150 to have most of the desired range of motion of the positioning apparatus 10 of the first embodiment.

Instead of being composed of plastic and being flat and rectangular in shape, the arm, upper torso, lower torso, and leg stiffeners 152–158 may be composed of metal and/or be tubular in shape.

It should be appreciated that the second positioning apparatus 150 may be connected by the valve complex 86 to the vacuum source 88 and the pressure source 90 in the same manner as the positioning apparatus 10, as described above.

Figure 9:
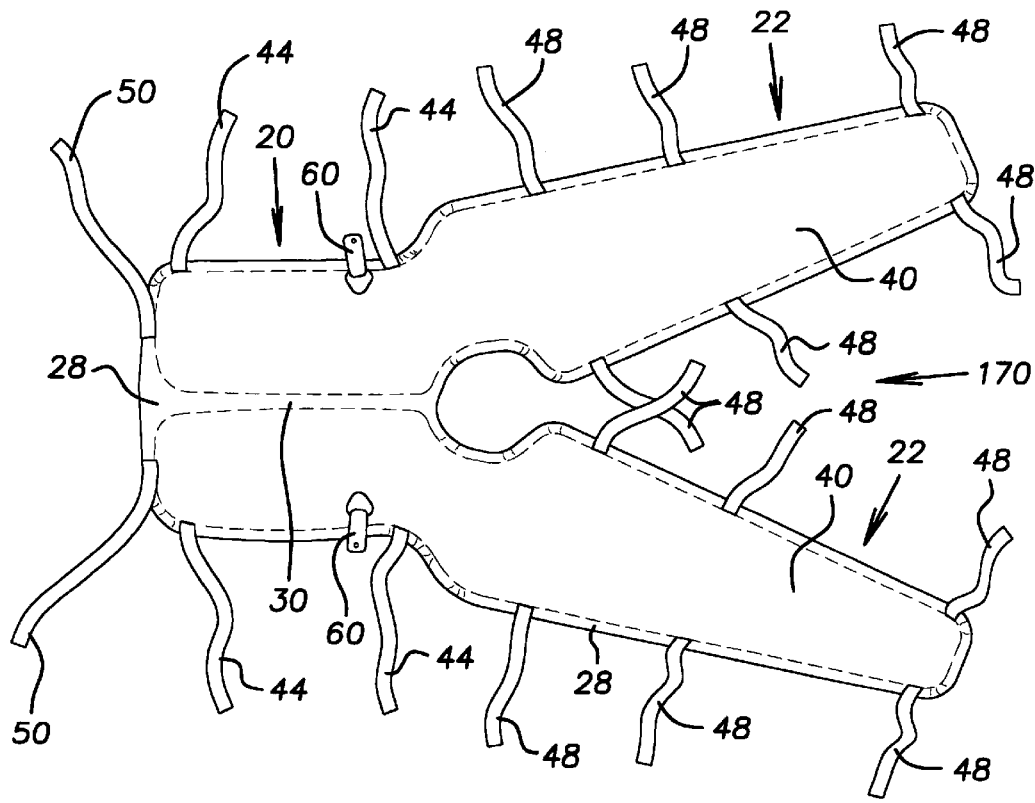
FIG. 9 shows a rear view of a third embodiment of the positioning apparatus.
Figure 10:
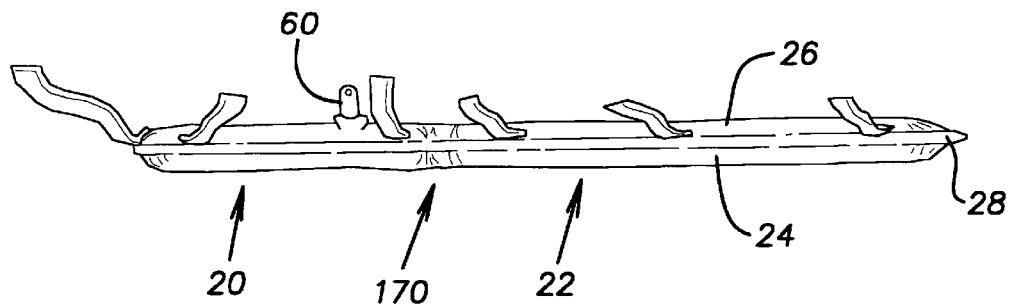
FIG. 10 shows a side view of the third embodiment of the positioning apparatus.

Referring now to FIGS. 9 and 10, there is shown a third embodiment of the present invention. Specifically, FIGS. 9 and 10 shows a third positioning apparatus 170 having essentially the same construction as the positioning apparatus 10 of the first embodiment, except for the differences to be hereinafter described. The third positioning apparatus 170 does not have the head section 14, the arm sections 16, the upper torso section 18, or the middle transverse seal 32 of the positioning apparatus 10 of the first embodiment, thereby giving the third positioning apparatus 170 the general shape of a pair of trousers.

In the third positioning apparatus 170, the peripheral seal 28 extends laterally across the top of the lower torso section 20. In addition, the anchor straps 50 have been moved upward so as to be located at the peripheral seal 28. Although not shown, the third positioning apparatus 170 may include the leg stiffeners 158 and the lower torso stiffeners 156 of the second embodiment.

The third positioning apparatus 170 is especially suited for use in medical procedures that are performed only on the lower extremities of a patient, such as gynecological and obstetrical procedures, and orthopedic procedures on the feet and the legs.

Figures 11, 12:
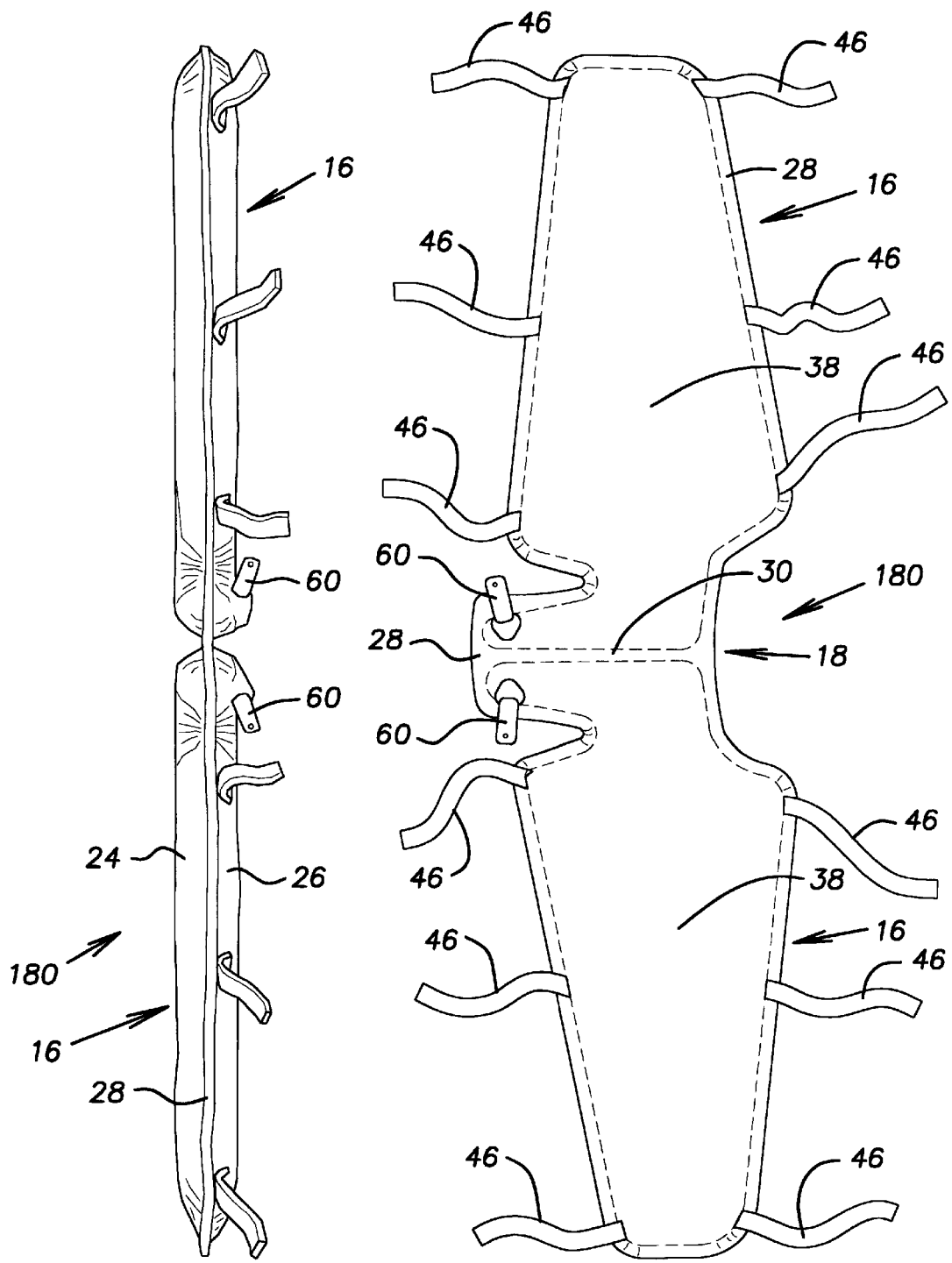
FIG. 11 shows a rear view of a fourth embodiment of the positioning apparatus.
FIG. 12 shows a side view of the fourth embodiment of the positioning apparatus.

Referring now to FIGS. 11 and 12, there is shown a fourth embodiment of the present invention. Specifically, FIGS. 11 and 12 shows a fourth positioning apparatus 180 having essentially the same construction as the positioning apparatus 10 of the first embodiment, except for the differences to be hereinafter described. The fourth positioning apparatus 180 does not have the head section 14, the upper transverse seal 34, or the middle transverse seal 32, the lower torso section 20, or the leg sections 22 of the positioning apparatus 10 of the first embodiment, thereby giving the fourth positioning apparatus 180 the general shape of a pair of wings.

In the fourth positioning apparatus 180, the peripheral seal 28 extends laterally across the top and bottom of the upper torso section 18. Although not shown, the fourth positioning apparatus 180 may include the arm stiffeners 152 and the upper torso stiffeners 154 of the second embodiment.

The fourth positioning apparatus 180 is especially suited for use in orthopedic procedures that are performed only on the arms or shoulders of a patient.

Figure 13:
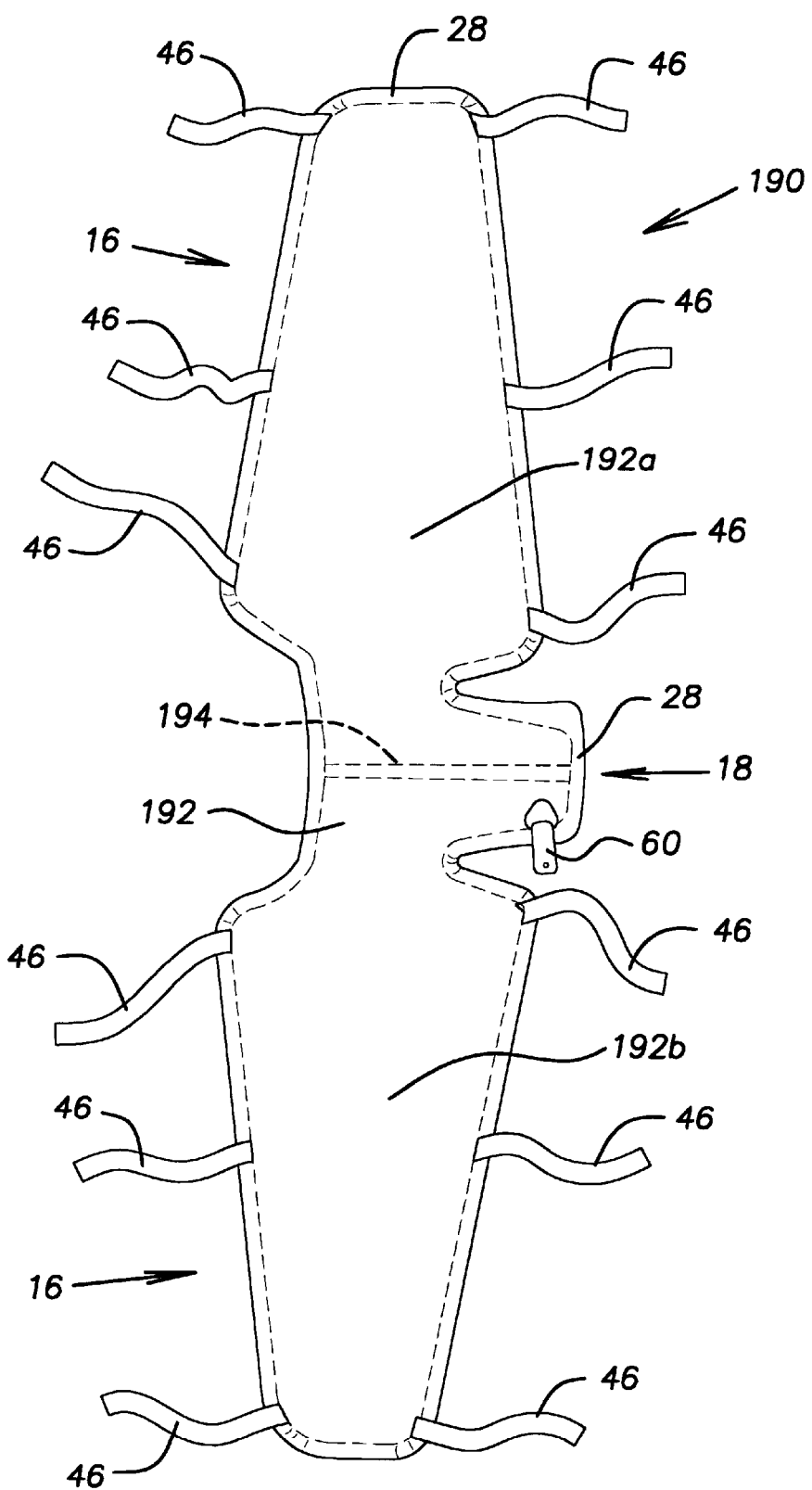
FIG. 13 shows a rear view of a fifth embodiment of the present invention.

Referring now to FIG. 13, there is shown a fifth embodiment of the present invention. Specifically, FIG. 13 shows a fifth positioning apparatus 190 having essentially the same construction as the fourth positioning apparatus 180 of the fourth embodiment, except for the differences to be hereinafter described. The longitudinal seal 30 has been removed, thereby creating a single enlarged arm compartment 192 that occupies both of the arm sections 16. The enlarged arm compartment 192 contains only one connection port 60 through which air may be evacuated from the enlarged arm compartment 192. An air permeable baffle 194 may be disposed in the enlarged arm compartment 192 in the upper torso section 18, between the arm sections 16, so as to divide the enlarged air compartment 192 into two portions 192a, 192b. The baffle 194 permits air, but not the beads 58 to pass through the baffle 194. In this manner, the baffle 194 prevents all of the beads 58 from accumulating in one arm section 16, while permitting both portions 192a, 192b of the enlarged arm compartment 192 to be evacuated from the single connection port 60.

It should be appreciated that the third positioning apparatus 170, the fourth positioning apparatus 180, and the fifth positioning apparatus 190 may be connected to the vacuum source 88 and the pressure source 90 using the valve complex 86, modified as needed to account for the reduction in the number of compartments.

Although the preferred embodiments of this invention has been shown and described, it should be understood that various modifications and rearrangements of the parts may be resorted to without departing from the scope of the invention as disclosed and claimed herein.

What is claimed is:

1. A positioning apparatus for positioning a patient for a medical procedure, said positioning apparatus comprising:

an air-impervious casing having a plurality of sections with compartments formed therein, said compartments being sealed from each other to prevent air flow therebetween;

a plurality of beads disposed in the compartments; and a plurality of connection ports through which air can be evacuated from the compartments to form vacuums therein; and wherein when the compartments are not at a vacuum, the beads in the compartments are free to move relative to each other, and when the compartments are at a vacuum, the beads in the compartments are compacted together.

2. The positioning apparatus of claim 1, wherein the sections of the casing include limb sections adapted to position limbs of the patient.

3. The positioning apparatus of claim 2, further comprising a plurality of limb straps secured to the casing and adapted to secure the limbs to the limb sections.

4. The positioning apparatus of claim 3, further comprising anchor straps secured to the casing and adapted to secure the positioning apparatus to a structure.

5. The positioning apparatus of claim 2, wherein the limbs are arms, and the limb sections are arm sections.

6. The positioning apparatus of claim 2, wherein the limbs are legs, and the limb sections are leg sections.

7. The positioning apparatus of claim 2, wherein the limbs are a pair of legs and a pair of arms, and wherein the limb sections are a pair of leg sections and a pair of arm sections.

8. The positioning apparatus of claim 7, wherein the arm sections and the leg sections are spaced apart so as to permit the arm sections to position the arms when the leg sections are positioning the legs.

9. The positioning apparatus of claim 8, wherein the sections further include:

an upper torso section connected between the arm sections;

a head section connected to the upper torso section; and a lower torso section connected between the upper torso section and the leg sections.

10. The positioning apparatus of claim 9, wherein the compartments include:

a head compartment disposed in the head section;

arm compartments disposed in the arm sections and the upper torso section; and leg compartments disposed in the leg sections and the lower torso section.

11. The positioning apparatus of claim 1, further comprising valves disposed in the connection ports for opening and closing the connection ports.

12. The positioning apparatus of claim 1, further comprising:

a vacuum source for evacuating air from the compartments;

a pressure source for supplying air to the compartments; and a plurality of valves respectively connected to the connection ports, each of said valves being operable to selectively close an associated one of the connection ports, connect the associated one of the connection ports to the vacuum source, and connect the associated one of the connection ports to the pressure source.

13. A positioning apparatus for positioning a patient for a medical procedure, said positioning apparatus comprising:

an air-impervious casing having a pair of limb sections adapted to position a pair of limbs of the patient said casing having a pair of independent interior compartments;

a plurality of beads disposed inside the casing, said independent interior compartments containing at least a portion of the beads; and a connection port;

a second connection port; and wherein the connection port and the second connection port permit air to be respectively evacuated from the interior compartments to form vacuums therein, and when a vacuum is not formed inside the casing, the beads are free to move relative to each other, thereby making the limb sections flexible and movable relative to each other, and when a vacuum is formed inside the casing, at least a portion of the beads are compacted together, thereby making at least one of the limb sections of the casing rigid.

14. The positioning apparatus of claim 13, further comprising a plurality of limb straps secured to the casing and adapted to secure the limbs of the patient to the limb sections.

15. The positioning apparatus of claim 13 wherein the limbs are arms, and the limb sections are arm sections.

16. The positioning apparatus of claim 13, further comprising a second connection port; and wherein the casing has a pair of independent interior compartments containing at least a portion of the beads; and wherein the connection port and the second connection port permit air to be respectively evacuated from the interior compartments to form vacuums therein.

17. The positioning apparatus of claim 13, further comprising a second pair of limb sections adapted to position a second pair of limbs of the patient.

18. The positioning apparatus of claim 13, further comprising a valve disposed in the connection port for opening and closing the connection port.

19. A positioning apparatus for positioning a patient for a medical procedure, said positioning apparatus comprising:

an air-impervious casing having a plurality of sections with compartments formed therein;

a plurality of beads disposed in the compartments;

a plurality of connection ports through which air can be evacuated from the compartments to form vacuums therein;

a vacuum source for evacuating air from the compartments;

a pressure source for supplying air to the compartments; and a plurality of valves respectively connected to the connection ports, each of said valves being operable to selectively close an associated one of the connection ports, connect the associated one of the connection ports to the vacuum source, and connect the associated one of the connection ports to the pressure source; and wherein when the compartments are not at a vacuum, the beads in the compartments are free to move relative to each other, thereby making the sections flexible, and when the compartments are at a vacuum, the beads in the compartments are compacted together, thereby making the sections rigid.

20. The positioning apparatus of claim 19, wherein the pressure source is a vent to atmospheric pressure.

21. The positioning apparatus of claim 19, wherein the pressure source comprises a diverter valve connected to an atmospheric vent and a compressed air source, said diverter valve being operable to selectively connect the valve to the vent and the pressure source.

22. The positioning apparatus of claim 19, wherein the compartments are sealed from each other to prevent air flow therebetween.

23. A positioning apparatus for positioning a patient for a medical procedure, said positioning apparatus comprising:

an air-impervious casing having a torso section, and a limb section adapted to position a limb of the patient, said sections each containing a compartment, said compartments being sealed from each other to prevent air flow therebetween;

a torso stiffener secured to the torso section;

a limb stiffener secured to the limb section and movably connected to the torso stiffener;

a plurality of beads disposed inside the casing; and a connection port through which air can be evacuated from inside the casing to form a vacuum therein; and wherein when a vacuum is not formed inside the casing, the beads are free to move relative to each other, and when a vacuum is formed inside the casing, at least a portion of the beads are compacted together.

24. The positioning apparatus of claim 23, wherein the limb stiffener is connected to the torso stiffener by a ball joint.

25. The positioning apparatus of claim 23, wherein the limb stiffener is composed of plastic and has a living hinge formed therein.

26. The positioning apparatus of claim 23, wherein the limb is an arm, and the limb section is an arm section.

27. The positioning apparatus of claim 23, wherein the limb is a leg, and the limb section is a leg section.

28. A method of positioning a patient for a medical procedure, said method comprising the steps of:

providing a positioning apparatus comprising an air-impervious casing having at least first and second sections, said casing having a plurality of beads disposed therein;

securing the first section of the casing to a first portion of the patient;

securing the second section of the casing to a second portion of the patient;

moving the first and second sections relative to each other; and removing air from inside the casing to form a vacuum therein, said vacuum causing at least a portion of the beads inside the casing to compact together, thereby making at least one of the first and second sections of the casing rigid.

29. The method of claim 28, wherein the casing further comprises a third section; and wherein the method further comprises the step of securing the third section of the casing to a third portion of the patient.

30. The method of claim 29, wherein the first and third portions of the patient are legs of the patient, and the second portion of the patient is a torso of the patient.

31. The method of claim 29, wherein the first and third portions of the patient are arms of the patient, and the second portion of the patient is a torso of the patient.

32. The method of claim 29, wherein first, second, and third compartments are respectively disposed in the first, second, and third sections of the casing, said first, second, and third compartments each containing a portion of the beads and being independent from each other.

33. The method of claim 32, wherein air is only removed from one of said first, second, and third compartments.

* * * * *